United States Patent
Senaratne et al.

(10) Patent No.: US 12,404,529 B2
(45) Date of Patent: Sep. 2, 2025

(54) PROCESS FOR CONTROLLING ORGANIC ACID RATIOS IN A CARBON DIOXIDE BIOCONVERSION PROCESS

(71) Applicant: JUPENG BIO (HK) LIMITED, Hong Kong (CN)

(72) Inventors: Ryan Senaratne, Fayetteville, AR (US); Brandon Beard, Fayetteville, AR (US)

(*) Notice: Subject to any disclaimer, the term of this patent is extended or adjusted under 35 U.S.C. 154(b) by 0 days.

(21) Appl. No.: 18/631,515

(22) Filed: Apr. 10, 2024

(65) Prior Publication Data

US 2024/0287552 A1    Aug. 29, 2024

Related U.S. Application Data

(62) Division of application No. 17/159,614, filed on Jan. 27, 2021, now Pat. No. 11,981,950.

(60) Provisional application No. 62/967,220, filed on Jan. 29, 2020.

(51) Int. Cl.
*C12P 7/52* (2006.01)
*C12P 7/54* (2006.01)

(52) U.S. Cl.
CPC .. *C12P 7/52* (2013.01); *C12P 7/54* (2013.01)

(58) Field of Classification Search
CPC ..................................... C12P 7/54; C12P 7/52
See application file for complete search history.

(56) References Cited

U.S. PATENT DOCUMENTS 6,340,581 B1 * 1/2002 Gaddy .................. C12M 29/04
435/163

OTHER PUBLICATIONS

Kantzow, Christina, Alexander Mayer, and Dirk Weuster-Botz. "Continuous gas fermentation by Acetobacterium woodii in a submerged membrane reactor with full cell retention." Journal of biotechnology 212 (2015): 11-18. (Year: 2015).*

* cited by examiner

*Primary Examiner* — Robert J Yamasaki
(74) *Attorney, Agent, or Firm* — Mengqi Zheng; James P. Krueger

(57) ABSTRACT

A process includes providing a gaseous substrate comprising $CO_2$ to a bioreactor; providing acetogenic bacteria and medium to the bioreactor to provide a fermentation broth; providing sodium ions to the bioreactor through one or more sodium ion sources; fermenting the gaseous substrate with the acetogenic bacteria in the fermentation broth to produce one or more organic acids; and controlling a butyric acid to an acetic acid ratio by controlling the pH of the fermentation broth. In one aspect, butyric acid to acetic acid ratio increases when the pH of the fermentation broth decreases, and the ratio of butyric acid to acetic acid concentration decreases when the pH of the fermentation broth increases. The acetogenic bacteria includes a sodium translocating ATPase that is active during fermentation in the bioreactor. The sodium ions are provided so that $Na^+$ is maintained between 1000 to 11000 ppm (g/g) in culture broth.

19 Claims, 7 Drawing Sheets

PROCESS FOR CONTROLLING ORGANIC ACID RATIOS IN A CARBON DIOXIDE BIOCONVERSION PROCESS

This application is a divisional of U.S. application Ser. No. 17/159,614 filed Jan. 17, 2021, which claims the benefit of U.S. Provisional Application No. 62/967,220, filed Jan. 29, 2020, both of which are is incorporated in their its entirety herein by reference.

A process is provided for controlling organic acid ratios in a carbon dioxide bioconversion process. More specifically, the process includes providing a carbon dioxide containing gaseous stream to acetogenic bacteria and maintaining pH levels that provide desired ratios of organic acids. The process provides for high levels of carbon dioxide conversions, utilization of hydrogen and production of organic acids, including butyric acid.

BACKGROUND

Carbon dioxide generation occurs from natural processes as well as industrial processes that include combustion of fossil fuels such as coal, oil and natural gas. Due in part to industrial processes, atmospheric carbon dioxide concentration continues to increase. These increases in carbon dioxide concentration may contribute to atmospheric changes which result in climate change and global warming. Carbon dioxide is difficult to utilize in biological processes because of its highly oxidized state.

In addition to carbon dioxide, many industrial processes also result in production of hydrogen. Hydrogen has a high level of reducing potential. However, hydrogen is difficult to store and utilize due to its very flammable nature.

Bacterial fermentation system that can convert carbon dioxide to organic acids with the aid of hydrogen can have a big impact on efforts to minimize the release of carbon dioxide through human activities to the environment.

SUMMARY

A process includes providing a gaseous substrate comprising $CO_2$ to a bioreactor; providing acetogenic bacteria and medium to the bioreactor to provide a fermentation broth; providing sodium ions to the bioreactor through one or more sodium ion sources; fermenting the gaseous substrate with the acetogenic bacteria in the fermentation broth to produce one or more organic acids; and controlling a butyric acid to an acetic acid ratio by controlling the pH of the fermentation broth. In one aspect, a butyric acid to acetic acid ratio increases when the pH of the fermentation broth decreases, and the ratio of butyric acid to acetic acid concentration decreases when the pH of the fermentation broth increases. The acetogenic bacteria includes a sodium translocating ATPase that is active during fermentation in the bioreactor. The sodium ions are provided so that $Na^+$ is maintained between 1000 to 11000 ppm (g/g) in culture broth.

In another aspect, a process includes providing a gaseous substrate comprising $CO_2$ to a bioreactor; providing acetogenic bacteria and medium to the bioreactor to provide a fermentation broth; providing sodium ions to the bioreactor through one or more sodium ion sources; maintaining a pH of 6 or less in the fermentation broth; and fermenting the gaseous substrate with the acetogenic bacteria in the fermentation broth to produce one or more organic acids. In one aspect, maintaining a pH of 6 or less in the fermentation broth provides a ratio of butyric acid to acetic acid concentration of 0.2 or more. The acetogenic bacteria includes a sodium translocating ATPase that is active during fermentation in the bioreactor. The sodium ions are provided so that $Na^+$ is maintained between 1000 to 11000 ppm (g/g) in culture broth.

In another aspect, a process includes providing a gaseous substrate comprising $CO_2$ to a bioreactor; providing acetogenic bacteria and medium to the bioreactor to provide a fermentation broth; providing sodium ions to the bioreactor through one or more sodium ion sources; maintaining a pH of 6 or less in the fermentation broth; and fermenting the gaseous substrate with the acetogenic bacteria in the fermentation broth to produce one or more organic acids containing 3 or more carbon atoms. The acetogenic bacteria includes a sodium translocating ATPase that is active during fermentation in the bioreactor. The sodium ions are provided so that $Na^+$ is maintained between 1000 to 11000 ppm (g/g) in culture broth.

BRIEF DESCRIPTION OF FIGURES

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

Figure 1:
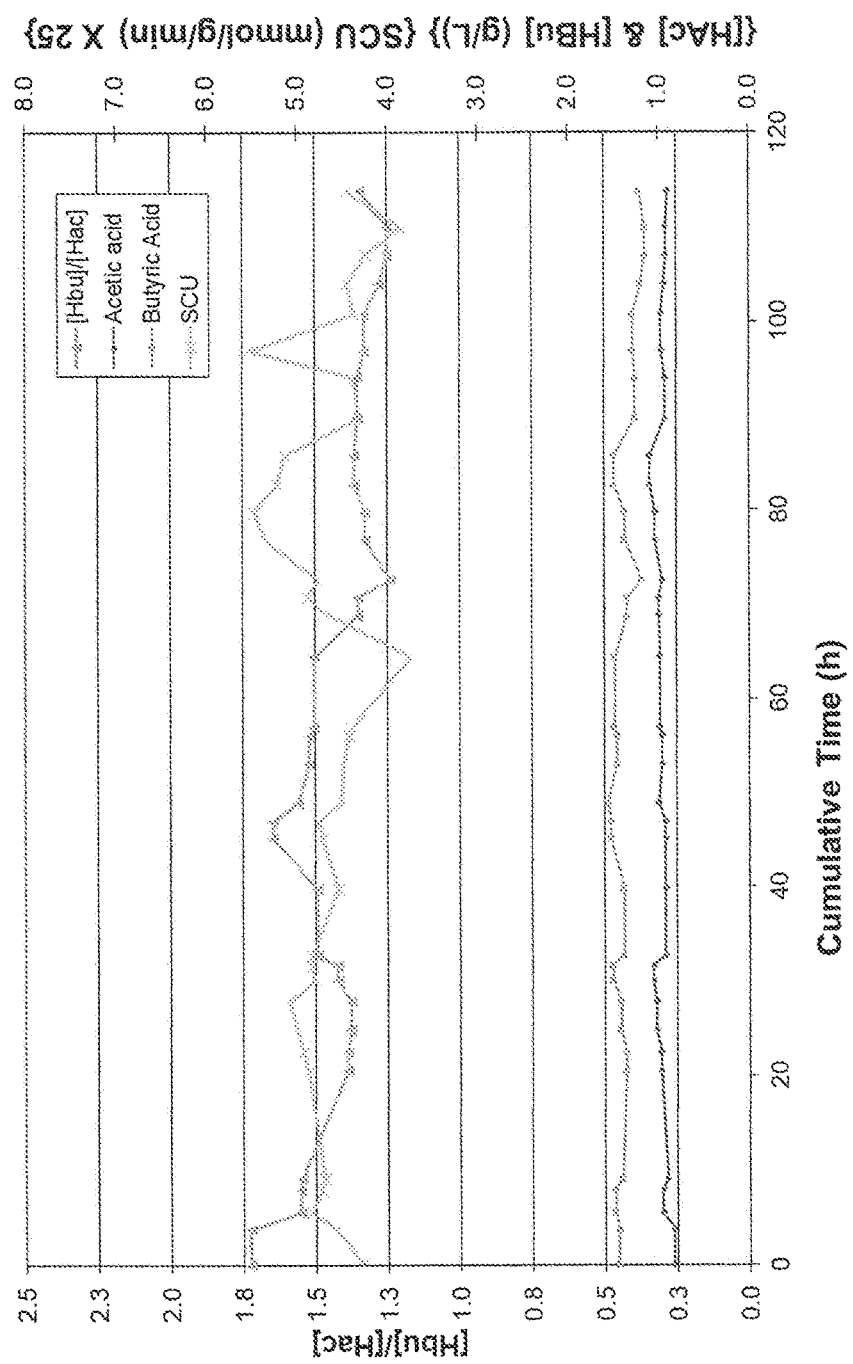
FIG. 1 illustrates acetic acid and butyric acid production by *Acetobacterium woodii* at pH 5.4 with $CO_2$ and $H_2$.

The following description is not to be taken in a limiting sense, but is made merely for the purpose of describing the general principles of exemplary embodiments. The scope of the disclosure should be determined with reference to the claims.

Definitions

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "fermentor" includes a fermentation device/bioreactor consisting of one or more vessels and/or towers or piping arrangements, which includes a batch reactor, semi-batch reactor, continuous reactor, continuous stirred tank reactor (CSTR), bubble column reactor, external circulation loop reactor, internal circulation loop reactor, immobilized cell reactor (ICR), trickle bed reactor (TBR), moving bed biofilm reactor (MBBR), gas lift reactor, membrane reactor such as hollow fibre membrane bioreactor (HFMBR), static mixer, gas lift fermentor, or other vessel or other device suitable for gas-liquid contact.

The terms "fermentation", fermentation process" or "fermentation reaction" and the like are intended to encompass both the growth phase and product biosynthesis phase of the process. In one aspect, fermentation refers to conversion of $CO_2$ to acetic acid and/or butyric acid.

The term "cell density" means mass of microorganism cells per unit volume of fermentation broth, for example, grams/liter.

The term "specific carbon uptake" means an amount of CO and $CO_2$ in millimoles (mmol) consumed by unit mass of microorganism cells (g) per unit time in minutes, i.e. mmole/gram/minute.

As used herein, productivity is expressed as STY. In this aspect, alcohol productivity may be expressed as STY (space time yield expressed as g ethanol/(L'day) or (g acetic acid/(L day) or (g butyric acid/(L day).

$CO_2$-Containing Gaseous Substrate

In one aspect, the process includes providing a $CO_2$-containing gaseous substrate to a bioreactor. A $CO_2$-containing substrate may include any gas that includes $CO_2$. In this aspect, a $CO_2$-containing gas may include industrial gases, fermentor gas streams including for example, fermentor off-gases and mixtures thereof. In a related aspect, the $CO_2$-containing substrate may include hydrogen or it may be blended with a hydrogen source to provide desired levels and ratios of $H_2$ to $CO_2$.

Industrial gases: In one aspect, the process includes providing a $CO_2$-containing gaseous substrate to a bioreactor where the $CO_2$-containing gaseous substrate is generated from industrial gases. Some examples of industrial gases include steel mill gas, industrial flue gas and incinerator exhaust gas. Examples of industrial gases include gases produced during ferrous metal products manufacturing, non-ferrous products manufacturing, petroleum refining processes, gasification of coal, gasification of biomass, electric power production, carbon black production, ammonia production, methanol production and coke manufacturing. Sources of hydrogen may include fossil fuels, steam reforming, oxidation of methane, coal gasification, and water electrolysis.

Depending on the composition of the gaseous $CO_2$-containing substrate, it may also be desirable to treat it to remove any undesired impurities, such as dust particles before introducing it to the fermentation. For example, the gaseous substrate may be filtered or scrubbed using known methods. Further, depending on the composition of the gaseous $CO_2$-containing substrate, the process may include adjusting the $CO_2$-containing substrate to increase or decrease concentrations of $CO_2$ and/or $H_2$ to fall within desired ranges.

Fermentor Gas Streams: In one aspect, the process includes providing a $CO_2$-containing substrate to a bioreactor where the $CO_2$-containing substrate is a fermentor gas stream. Some examples of fermentor gas streams include fermentor off-gas generated in the fermentation of syngas. Some examples of syngas fermentation are described in U.S. Pat. No. 7,285,402, filed Jul. 23, 2001, which is incorporated herein by reference.

In one aspect, the process has applicability to supporting the production of alcohol from gaseous substrates such as high volume CO-containing industrial flue gases. In some aspects, a gas that includes CO is derived from carbon containing waste, for example, industrial waste gases or from the gasification of other wastes. The fermentation of CO-containing gas may result in $CO_2$ in fermentor off-gas. As such, the processes represent effective processes for capturing carbon that would otherwise be exhausted into the environment. In this aspect, the off-gas from the fermentation of CO-containing gas may include about 0.5 mole % to about 50 mole % CO. In another aspect, the off-gas from the fermentation of CO-containing gas may include about 10 mole % to about 99.5 mole % $CO_2$, in another aspect, about 10 mole % to about 90 mole % $CO_2$, in another aspect, about 10 mole % to about 80 mole % $CO_2$, in another aspect, about 10 mole % to about 70 mole % $CO_2$, in another aspect, about 10 mole % to about 50 mole % $CO_2$, in another aspect, about 10 mole % to about 40 mole % $CO_2$, in another aspect, about 20 mole % to about 90 mole % $CO_2$, in another aspect, about 20 mole % to about 80 mole % $CO_2$, in another aspect, about 20 mole % to about 70 mole % $CO_2$, in another aspect, about 20 mole % to about 50 mole % $CO_2$, in another aspect, about 40 mole % to about 90 mole % $CO_2$, in another aspect, about 40 mole % to about 80 mole % $CO_2$, in another aspect, about 40 mole % to about 70 mole % $CO_2$, in another aspect, about 50 mole % to about 90 mole % $CO_2$, and in another aspect, about 50 mole % to about 80 mole % $CO_2$.

Blending of gas streams: According to particular aspects, streams from two or more sources can be combined and/or blended to produce a desirable and/or optimized substrate stream. For example, a stream comprising a high concentration of $CO_2$, such as the exhaust from a steel mill, can be combined with a stream comprising high concentrations of $H_2$, such as the off-gas from a steel mill coke oven.

Depending on the composition of the $CO_2$-containing substrate, the $CO_2$-containing substrate may be provided directly to a fermentation process or may be further modified to include an appropriate $H_2$ to $CO_2$ molar ratio. The $CO_2$-containing substrate may include from about 5 to about 90 mole % $CO_2$ and from about 5 to about 90 mole % $H_2$. In one aspect, the $CO_2$ containing gas stream includes about 5 to about 66.6% $CO_2$.

In another aspect, the $CO_2$-containing substrate may include from about 0 mole % to about 50 mole % CO, in another aspect, about 0.5 mole % CO to about 50 mole % CO, in another aspect, about 0.5 mole % CO to about 5 mole % CO, and in another aspect, about 2 mole % CO to about 5 mole % CO. In another aspect, the gaseous substrate has a CO to $CO_2$ ratio of less than about 2, in another aspect, less than about 1, in another aspect about 0 to about 2, in another aspect, less than about 0.5, in another aspect, less than about 0.3, in another aspect, less than about 0.2, and in another aspect, less than about 0.1.

In one aspect, the acetogenic bacteria will have a molar ratio of consumption of $H_2$ to $CO_2$ at a ratio of about 4:1 to about 1:2. Hence, any substrate gas provided to the bioreactor that includes $H_2$ and $CO_2$ can be utilized. However, optimal levels of substrate gas provided to the bioreactor will have a ratio of $H_2$ to $CO_2$ of about 4:1 to about 1:1, in another aspect, about 2:1, and in another aspect, about 3.5:1 to about 1.5:1.

Bioreactor Design and Operation

Descriptions of fermentor designs are described in U.S. Ser. Nos. 13/471,827 and 13/471,858, both filed May 15, 2012, U.S. Ser. No. 13/473,167, filed May 16, 2012, and U.S. Ser. Nos. 16/530,481 and 16/530,502, both filed Aug. 2, 2019, all of which are incorporated herein by reference.

The fermentation should desirably be carried out under appropriate conditions for the desired fermentation to occur (e.g. $CO_2$-to-acetic acid). Reaction conditions to considered include pressure, temperature, gas flow rate, liquid flow rate, medium pH, agitation rate (if using a stirred tank reactor), inoculum level, and maximum acetic acid concentration to avoid product inhibition. In this aspect, the process includes reaction conditions in the following ranges:

Pressure: about 0 to about 500 psi;
Temperature: about 30° C. to about 42° C.;
Medium pH: about 4 to about 6.9;
Agitation rate: about 100 to about 2000 rpm;
Nutrient supply as described herein.

Acetogenic Bacteria

In one aspect, the microorganisms utilized include acetogenic bacteria that include a sodium pump which may also be described as sodium-translocating ATPases (for membrane bioenergetics). Sodium-translocating ATPase are described in Muller, "Energy Conservation in Acetogenic Bacteria", Appl. Environ. Microbiol. November 2003, vol. 69, no. 11, pp. 6345-6353, which is incorporated herein by reference. The term sodium translocating ATPase may be used interchangeably with sodium dependent ATPase. Acetogens that include a sodium-translocating ATPase require about 500 ppm NaCl in their growth medium for growth. To determine if an acetogen includes a sodium-translocating ATPase, the acetogen is inoculated into a serum bottles containing about 30 to about 50 ml of growth medium with about 0 to about 2000 ppm NaCl. Optimum growth at NaCl concentrations of about 500 ppm or more indicates that the acetogen includes a sodium-translocating ATPase.

In this aspect, suitable microorganisms include *Acetobacterium* bacteria, *Acetogenium kivui, Acetoanaerobium noterae, Acetobacterium woodii, Alkalibaculum bacchi* CP11 (ATCC BAA-1772), *Moorella thermoacetica, Moorella thermoautotrophica, Ruminococcus productus*, and combinations thereof. In another aspect, the microorganism is *Acetobacterium woodii*.

Medium Compositions and Control of Medium Feed Rates

In accordance with one aspect, the fermentation process is started by addition of a suitable medium to the reactor vessel. The liquid contained in the reactor vessel may include any type of suitable nutrient medium or fermentation medium. The nutrient medium will include vitamins and minerals effective for permitting growth of the microorganism being used. Sterilization may not always be required.

Concentrations of various medium components are as follows:

| Element | Concentration mg/L | Feed Rate µg/gram cells/min |
|---|---|---|
| $NH_4^+$ | 82-3280 | 20.5-820 |
| Fe | 0.85-34 | 0.28-8.5 |
| Ni | 0.07-2.81 | 0.023-0.702 |
| Co | 0.037-1.49 | 0.012-0.373 |
| Se | 0.027-1.1 | 0.009-0.274 |
| Zn | 0.59-23.8 | 0.198-5.95 |
| Mo | 0.003-0.397 | 0.003-0.1 |
| chelator | 2.5-100 | 0.83-25 |
| W | 0.8-32.1 | 0.26-8.03 |
| K | 98-3933 | 32.77-983.35 |
| Mg | 0.71-28.69 | 0.23-7.18 |
| Na | 875-35000 | 290-8750 |
| S | 15-625 | 2.08-62.5 |
| P | 20-805 | 6.7-201.3 |
| d-biotin | 0.016-0.64 | 0.005-0.16 |
| thiamine HCl | 0.04-1.6 | 0.01-0.4 |
| calcium-D-pantothenate | 0.02-0.81 | 0.006-0.202 |

Vitamins solution contains d-biotin, thiamine HCl, and calcium-D-pantothenate.

0.5 M NaOH was used to maintain the pH of the culture around 4.5 to 6. The approximate usage of NaOH per gram of cells per hour was 0.1 to 0.4 ml/min per gram of cells.

Process operation maintains a pH in a range of about 4 to about 6.9, in another aspect, about 5 to about 6.5, in another aspect about 5.1 to about 6, and in another aspect, about 5.2 to about 6. The medium includes less than about 0.01 g/L yeast extract and less than about 0.01 g/L carbohydrates.

The composition also includes a sodium ion concentration of about 40 to about 500 mmol per liter, in another aspect, about 40 to about 250 mmol per liter and in another aspect, a sodium ion concentration of about 50 to about 200 mmol per liter. In one aspect, the sodium ion concentration is about 500 ppm to about 8000 ppm, in another aspect, about 1000 ppm to about 7000 ppm, in another aspect, about 3000 ppm to about 6000 ppm, in another aspect, about 2000 to about 5000 ppm Na, and in another aspect, about 3000 to about 4000 ppm Na. The sodium ion source is provided by a compound selected from the group consisting of sodium chloride, sodium hydroxide, sodium phosphate, sodium sulfate, sodium nitrate, sodium bicarbonate, sodium bisulfate and mixtures thereof.

The composition includes a source of molybdenum. In this aspect the molybdenum concentration is about 3.97 µg/L to about 396.5 µg/L, and in another aspect, about 7.93 µg/L to about 198.25 µg/L. Sources of molybdenum include $Na_2MoO_4$, $CaMoO_4$, $FeMoO_4$ and mixtures thereof.

The composition may also include a complexing agent. In this aspect, a complexing agent may be included in the composition when the composition has a pH of about 5.2 or greater. The complexing agent may include ethylenediaminetetraacetic acid (EDTA), ethylenediamine diacetic acid (EDDA), ethylenediamine disuccinic acid (EDDS), nitrilotriacetic acid (NTA), and mixtures thereof.

The composition may include one or more of a source of $NH_4^+$, P, K, Fe, Ni, Co, Se, Zn, or Mg. Sources of each of these elements may be as follows.

$NH_4^+$: The nitrogen may be provided from a nitrogen source selected from the group consisting of ammonium hydroxide, ammonium chloride, ammonium phosphate, ammonium sulfate, ammonium nitrate, and mixtures thereof.

P: The phosphorous may be provided from a phosphorous source selected from the group consisting of phosphoric acid, ammonium phosphate, potassium phosphate, and mixtures thereof.

K: The potassium may be provided from a potassium source selected from the group consisting of potassium chloride, potassium phosphate, potassium nitrate, potassium sulfate, and mixtures thereof.

Fe: The iron may be provided from an iron source selected from the group consisting of ferrous chloride, ferrous sulfate, and mixtures thereof.

Ni: The nickel may be provided from a nickel source selected from the group consisting of nickel chloride, nickel sulfate, nickel nitrate, and mixtures thereof.

Co: The cobalt may be provided from a cobalt source selected from the group consisting of cobalt chloride, cobalt fluoride, cobalt bromide, cobalt iodide, and mixtures thereof.

Se: The selenium may be provided from $Na_2SeO_3$, $C_3H_6NO_2Se$, and mixtures thereof.

Zn: The zinc may be provided from $ZnSO_4$.

W: The tungsten may be provided from a tungsten source selected from the group consisting of sodium tungstate, calcium tungstate, potassium tungstate, and mixtures thereof.

Mg: The magnesium may be provided from a magnesium source selected from the group consisting of magnesium chloride, magnesium sulfate, magnesium phosphate, and mixtures thereof.

S: The composition may also include sulfur. The sulfur may be provided from a sulfur source selected from the group consisting of cysteine, sodium sulfide, NaHS, $NaH_2S$ and mixtures thereof.

Upon inoculation, an initial feed gas supply rate is established effective for supplying the initial population of microorganisms. Effluent gas is analyzed to determine the content of the effluent gas. Results of gas analysis are used to control feed gas rates. In this aspect, the process provides a minimal cell density of about 0.1 grams per liter. In another aspect, the process provides a calculated $CO_2$ concentration (mmol/min) to initial cell density (g/L) ratio of about 0.05 to about 0.8, and in another aspect, about 0.01 to about 2.

In one aspect, nutrients may be added to the culture to increase cell growth rates. Suitable nutrients during inoculation may include non-carbohydrate fractions of yeast extract.

The fermentation process is effective for increasing cell density as compared to a starting cell density. Upon reaching desired levels, liquid phase and cellular material is withdrawn from the reactor and replenished with medium to maintain the desired cell density. In this aspect, the process provides an average cell density of about 2 to about 50 grams/liter, in another aspect, about 2 to about 30 grams/liter, in another aspect, about 2 to about 20 grams/liter, in another aspect, about 2 to about 10 grams/liter, and in another aspect, about 2 to about 6 grams/liter.

Production of Organic Acid: In another aspect, the process provides a source of organic acids. In this aspect, the process may include obtaining acid product or products from the fermentation liquid broth. In this aspect, provides a specific organic acid productivity of about 0.02 to about 50 grams organic acid/liter/day/g cells, in another aspect, about 0.02 to about 20 grams organic acid/liter/day/g cells, in another aspect, about 0.02 to about 10 grams organic acid/liter/day/g cells, in another aspect, about 0.02 to about 5 grams organic acid/liter/day/g cells, in another aspect, about 0.2 to about 50 grams organic acid/liter/day/g cells, in another aspect, about 10 to about 50 grams organic acid/liter/day/g cells, in another aspect, about 14 to about 30 grams organic acid/liter/day/g cells, in another aspect, about 2 to about 20 grams organic acid/liter/day/g cells and in another aspect, about 15 to about 25 grams organic acid/liter/day/g cells. In one aspect, the organic acid is acetic acid or butyric acid, or a mixture of both.

In one aspect, the process includes maintaining a pH of 6 or less in the fermentation broth to provide a ratio butyric acid to acetic acid concentration of 0.2 or more, in another aspect, about 0.5 or more, and in another aspect, about 0.1 or more. The process may provide a specific butyric acid productivity of about 0.5 to about 5 grams/liter/day/g cells, in another aspect, about 0.5 to about 4 grams/liter/day/g cells, in another aspect, about 1 to about 3 grams/liter/day/g cells, and in another aspect, about 1 to about 15 grams/liter/day/g cells.

In another aspect, the process includes maintaining a pH of 6 or less in the fermentation broth and fermenting the gaseous substrate with the acetogenic bacteria in the fermentation broth to produce one or more organic acids containing 3 or more carbon atoms. In one aspect, the organic acid is butyric acid or mixtures of butyric acid and propionic acid. The process may provide a specific butyric acid productivity of about 0.5 grams/liter/day/g cells or more. In another aspect, the process may provide a specific butyric acid productivity of about 0.5 to about 5 grams/liter/day/g cells, in another aspect, about 0.5 to about 4 grams/liter/day/g cells, in another aspect, about 1 to about 3 grams/liter/day/g cells, and in another aspect, about 1 to about 15 grams/liter/day/g cells.

Conversions of $CO_2$ and $H_2$: The process is effective for providing a $CO_2$ uptake of about 0.05 to about 3 mmol $CO_2$/minute/gram dry cells, an $H_2$ uptake of about 0.08 to about 3 mmol $H_2$/minute/gram dry cells. The process is effective for providing about 25 to about 100% conversion of $CO_2$, in another aspect, about 50 to about 100% conversion of $CO_2$, and in another aspect, about 75 to about 100% conversion of $CO_2$. In another aspect, the process is effective for providing about 25 to about 100% conversion of $H_2$, in another aspect, about 50 to about 100% conversion of $H_2$, and in another aspect, about 75 to about 100% conversion of $H_2$.

EXAMPLES

Example 1: Preparation of *Acetobacterium woodii*

An initial lyophilized pellet of *Acetobacterium woodii* was obtained from German culture collection DSMZ, strain ID DSM-1030. Culture was initially revived from lyophilized pellet using rich medium (fructose and yeast extract). An adaptation method was used to remove fructose from serum bottle medium where concentration of fructose in growth medium was stepped down 75%, 50%, 10%. Growth rate and gas usage was used as an indicator of adaptation. (approximately 5 weeks). Preliminary pH adaptation work in serum bottles reduced required pH from 7.4 to 6.0 (3 weeks). At this point, culture was amplified and inoculated into a reactor. In a reactor culture was further adapted to grow in lower pH of 5.2 to 5.7.

Example 2: CSTR Reactor Experiment for an *Acetobacterium Woodii* Culture Grown at pH 5.4 with $CO_2$ and $H_2$ A synthesis gas containing $CO_2$ and $H_2$ was continuously introduced into a stirred tank bioreactor containing *Acetobacterium woodii*, along with a conventional liquid nutrient medium containing vitamins, trace metals, cysteine (as sulfur source), and salts.

A New Brunswick Bioflow 310 reactor containing nutrient medium and actively growing *Acetobacterium woodii* was used in this experiment. The rate of agitation of the reactor was set to 600 rpm. This agitation rate remained constant throughout the experiment. Feed gas flow to the reactor was increased from an initial rate of 100 ml/min to 108 ml/min. Temperature in the bioreactor was maintained at 33.0° C. throughout the experiment. Na+ levels were kept at about 3500-4000 ppm. Samples of syngas feed into the bioreactor and off-gas from the bioreactor and fermentation broth in the bioreactor were taken at intervals, for example feed gas, off-gas and fermentation broth were sampled about daily, once every two hours and once every four hours respectively. Above samples were analyzed for consumption or production of various gas components, broth acetic acid concentration, and the optical density (cell density) of the culture. The unaroused volume of the reactor was maintained between 1900 to 2275 ml throughout the experiment. Also, the gas flow to the reactor was measured in real time by the mass flow controller regulating gas flow to the reactor. The feed gas composition of this experiment was 70% $H_2$, 25% $CO_2$ and 5% $N_2$.

In this experiment, a cell recycle system (CRS) was attached to the reactor before the start of the experiment. The rate of flow of nutrient medium to the reactor was 5.0 ml/min. Nutrient medium feed rate was maintained throughout the experiment.

In this experiment, $H_2$ and $CO_2$ in the feed gas was fixed into cell material, acetic acid and butyric acid. The removal of $H_2$ and $CO_2$ was calculated by comparing inlet gas composition with the effluent gas composition. Component gas uptake can be expressed in % of gas molecules converted by bacteria. In this experiment the following conversions were achieved; $H_2$: 51%-65%, $CO_2$: 61%-75%. In this experiment the rate of acetic acid production was 4.63 g/L/day, and the rate of butyric acid production was 6.65 g/L/day.

Results can be summarized as follows:

| | |
|---|---|
| Average Specific $CO_2$ uptake (mmol $CO_2$/min/gram dry cells) | 0.19 |
| Average Specific Acetic Acid productivity (g/L/day/g cells) | 1.78 |
| Average Specific Butyric Acid productivity (g/L/day/g cells) | 2.54 |
| Average Cell Density (g/L) | 2.63 |

Figure 2:
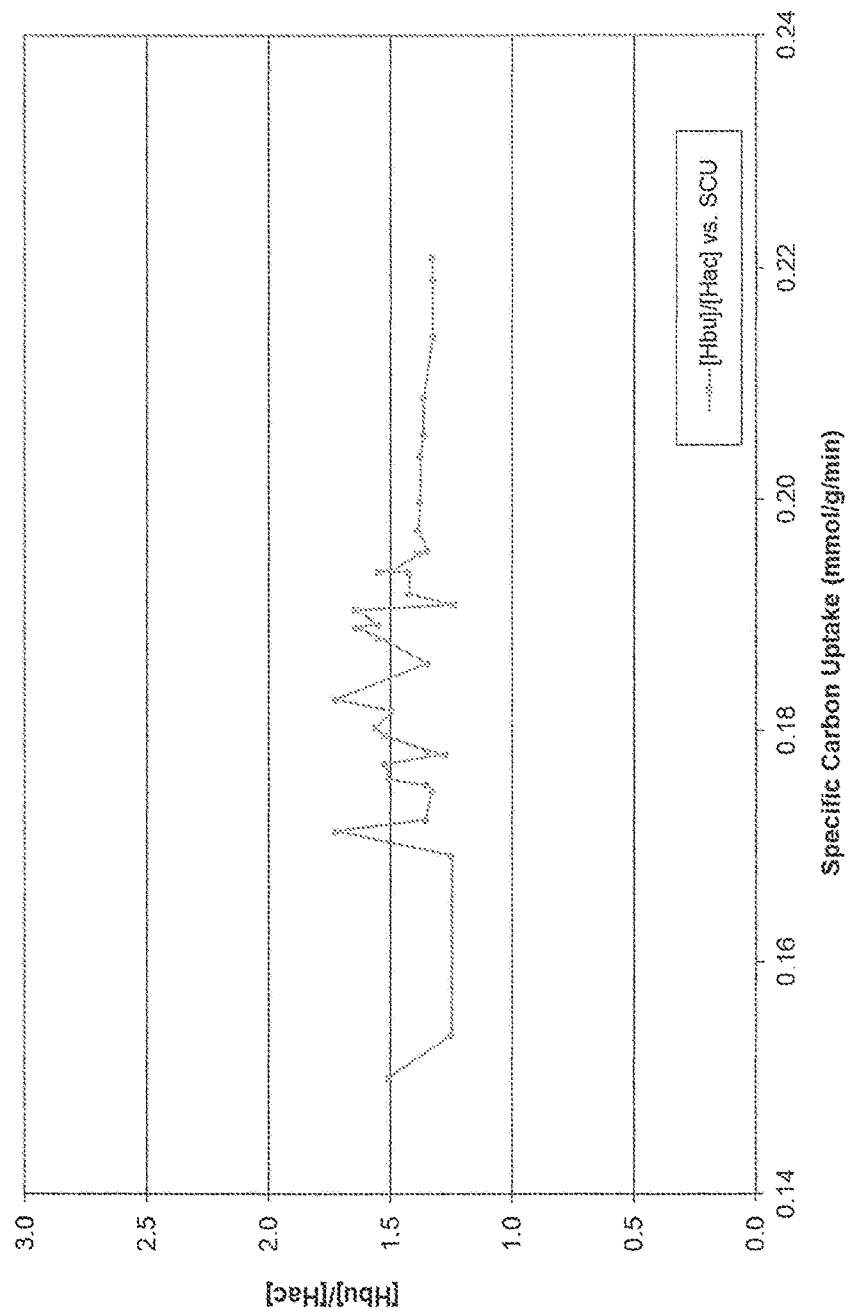
FIG. 2 shows a ratio of the concentration of butyric acid to the concentration of acetic acid versus specific carbon uptake by *Acetobacterium woodii* at pH 5.4 with $CO_2$ and $H_2$.

FIG. 1 illustrates acetic acid and butyric acid production at pH 5.4. FIG. 2 shows a ratio of the concentration of butyric acid to the concentration of acetic acid versus specific carbon uptake.

Example 3: CSTR Reactor Experiment for an *Acetobacterium woodii* Culture Grown at pH 5.4 with $CO_2$, CO and $H_2$ A synthesis gas containing $CO_2$, CO and $H_2$ was continuously introduced into a stirred tank bioreactor containing *Acetobacterium woodii*, along with a conventional liquid nutrient medium containing vitamins, trace metals, cystine (as sulfur source), and salts.

A New Brunswick Bioflow 310 reactor containing nutrient medium and actively growing *Acetobacterium woodii* was used in this experiment. The rate of agitation of the reactor was set to 600 rpm. This agitation rate remained constant throughout the experiment. Feed gas flow to the reactor was increased from an initial rate of 87 ml/min to 211 ml/min. Temperature in the bioreactor was maintained at 33.0° C. throughout the experiment. Na+ levels were kept at about 3500-4000 ppm. Samples of syngas feed into the bioreactor and off-gas from the bioreactor and fermentation broth in the bioreactor were taken at intervals, for example feed gas, off-gas and fermentation broth were sampled about daily, once every two hours and once every four hours respectively. Above samples were analyzed for consumption or production of various gas components, broth acetic acid concentration, and the optical density (cell density) of the culture. The unaroused volume of the reactor was maintained between 1900 to 2275 ml throughout the experiment. Also, the syngas flow to the reactor was measured in real time by the mass flow controller regulating syngas to the reactor. The feed syngas composition of this experiment was 62% $H_2$, 25% $CO_2$, 8% CO and 5% $N_2$.

In this experiment, a cell recycle system (CRS) was attached to the reactor before the start of the experiment. The rate of flow of nutrient medium to the reactor was 5.0 ml/min. Medium feed rate was maintained throughout the experiment.

In this experiment, $H_2$, CO and $CO_2$ in the feed gas was fixed into cell material, acetic acid and butyric acid. The removal of $H_2$, CO and $CO_2$ was calculated by comparing inlet gas composition with the effluent gas composition. Component gas uptake can be expressed in % of gas molecules converted by bacteria. In this experiment the following conversions were achieved; $H_2$: 35%-63%, CO: 84%-95%, $CO_2$: 16%-50%. In this experiment the rate of acetic acid production was 3.13 g/L/day, and the rate of butyric acid production was 3.18 g/L/day.

Results can be summarized as follows:

| | |
|---|---|
| Average Specific $CO_2$ uptake (mmol $CO_2$/min/gram dry cells) | 0.10 |
| Average Specific CO uptake (mmol CO/min/gram dry cells) | 0.14 |
| Average Specific Acetic Acid productivity (g/L/day/g cells) | 1.12 |
| Average Specific Butyric Acid productivity (g/L/day/g cells) | 1.57 |
| Average Cell Density (g/L) | 2.78 |

Figure 3:
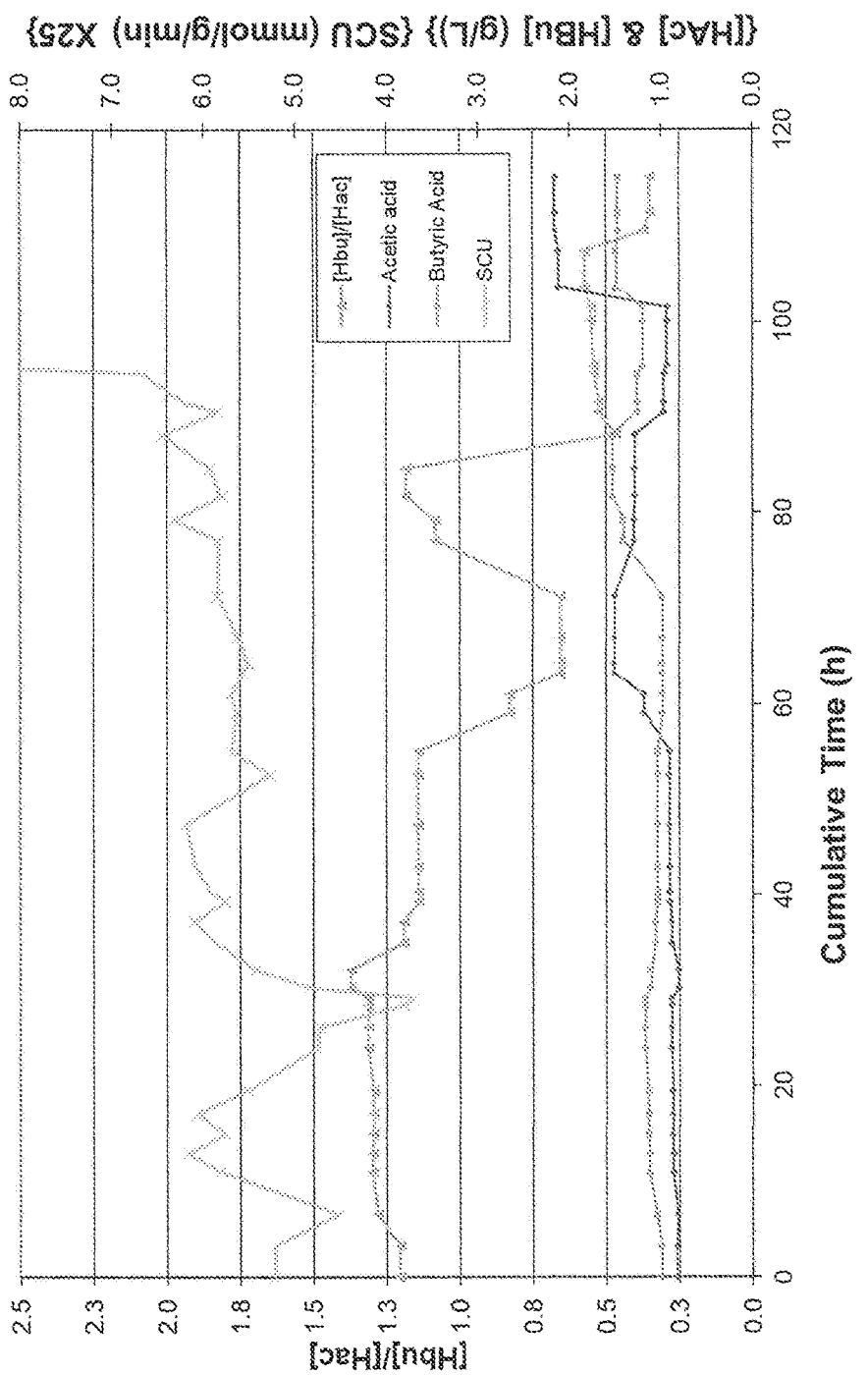
FIG. 3 describes acetic acid and butyric acid production by *Acetobacterium woodii* at pH 5.4 with $CO_2$, CO and $H_2$.
Figure 4:
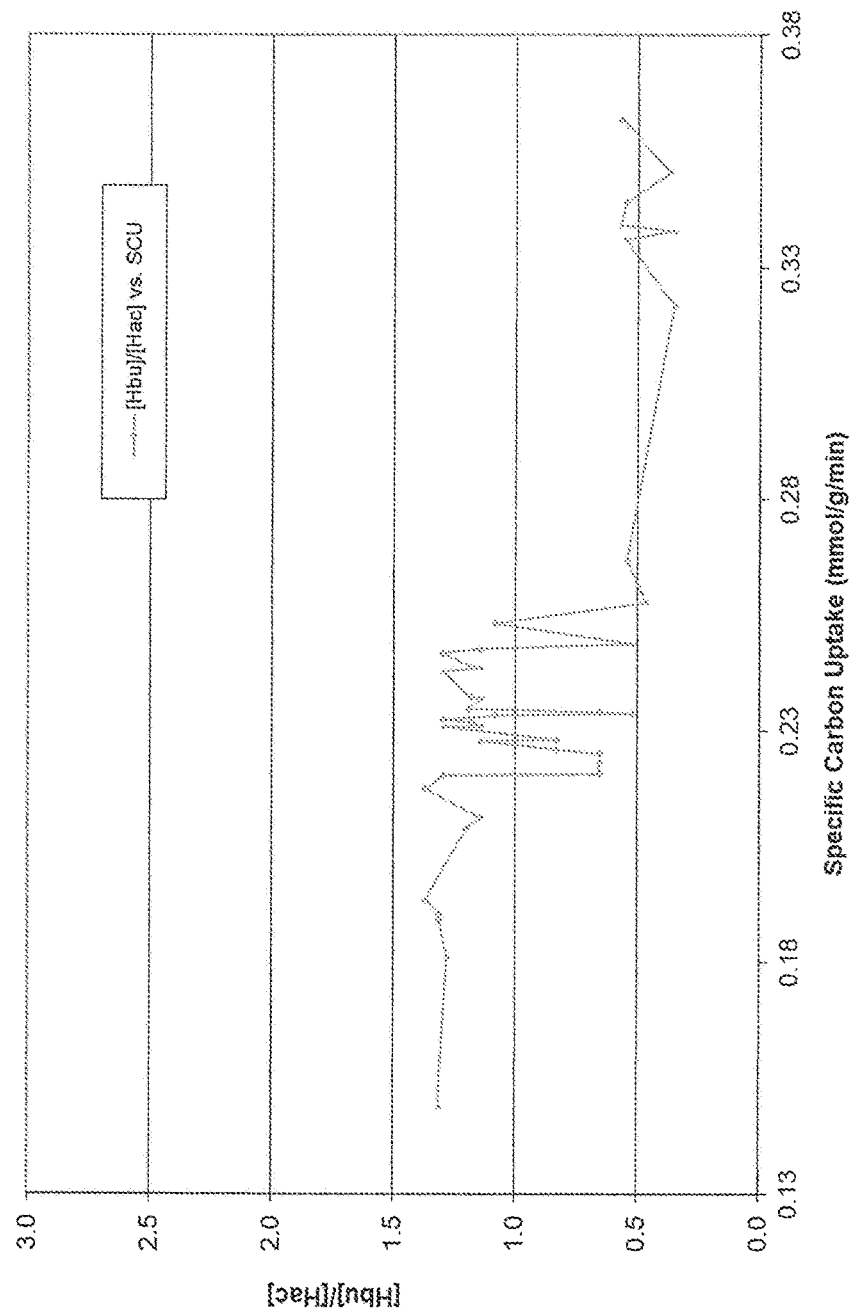
FIG. 4 shows a ratio of the concentration of butyric acid to the concentration of acetic acid versus specific carbon uptake by *Acetobacterium woodii* at pH 5.4 with $CO_2$, CO and $H_2$.

FIG. 3 illustrates acetic acid and butyric acid production at pH 5.4. FIG. 4 shows a ratio of the concentration of butyric acid to the concentration of acetic acid versus specific carbon uptake.

Example 4: CSTR Reactor Experiment for an *Acetobacterium woodii* Culture Grown at pH 6.1

A gas containing $CO_2$ and $H_2$ was continuously introduced into a stirred tank bioreactor containing *Acetobacterium woodii*, along with a conventional liquid nutrient medium containing vitamins, trace metals, cystine (as sulfur source), and salts.

A New Brunswick Bioflow 310 reactor containing nutrient medium and actively growing *Acetobacterium woodii* was used in this experiment. The rate of agitation of the reactor was set to 600 rpm. This agitation rate remained constant throughout the experiment. Feed gas flow to the reactor was maintained between 97 ml/min to 123 ml/min. Temperature in the bioreactor was maintained at 33.0° C. throughout the experiment. Na+ levels were kept at about 3500-4000 ppm. Samples of syngas feed into the bioreactor and off-gas from the bioreactor and fermentation broth in the bioreactor were taken at intervals, for example feed gas, off-gas and fermentation broth were sampled about daily, once every two hours and once every four hours respectively. Above samples were analyzed for consumption or production of various gas components, broth acetic acid concentration, and the optical density (cell density) of the culture. The unaroused volume of the reactor was maintained between 1900 to 2275 ml throughout the experiment. Also the gas flow to the reactor was measured in real time by the mass flow controller regulating gas to the reactor. The feed gas composition of this experiment was 70% $H_2$, 25% $CO_2$ and 5% $N_2$.

In this experiment, a cell recycle system (CRS) was attached to the reactor before the start of the experiment. During the experiment, the rate of flow of nutrient medium to the reactor was 3.5-5.0 ml/min. Medium feed rate was maintained throughout the experiment.

In this experiment, $H_2$ and $CO_2$ in the feed gas was fixed into cell material, acetic acid and butyric acid. The removal of $H_2$ and $CO_2$ was calculated by comparing inlet gas composition with the effluent gas composition. Component gas uptake can be expressed in % of gas molecules converted by bacteria. In this experiment the following conversions was achieved; $H_2$: 29%-70%, $CO_2$: 40%-86%. In this experiment the rate of acetic acid production was 22.8 g/L/day, and the rate of butyric acid production was 2.67 g/L/day.

Results can be summarized as follows:

| | |
|---|---|
| Average Specific $CO_2$ uptake (mmol $CO_2$/min/gram dry cells) | 0.23 |
| Average Specific Acetic Acid productivity (g/L/day/g cells) | 7.93 |
| Average Specific Butyric Acid productivity (g/L/day/g cells) | 0.21 |
| Average Cell Density (g/L) | 3.00 |

Figure 5:
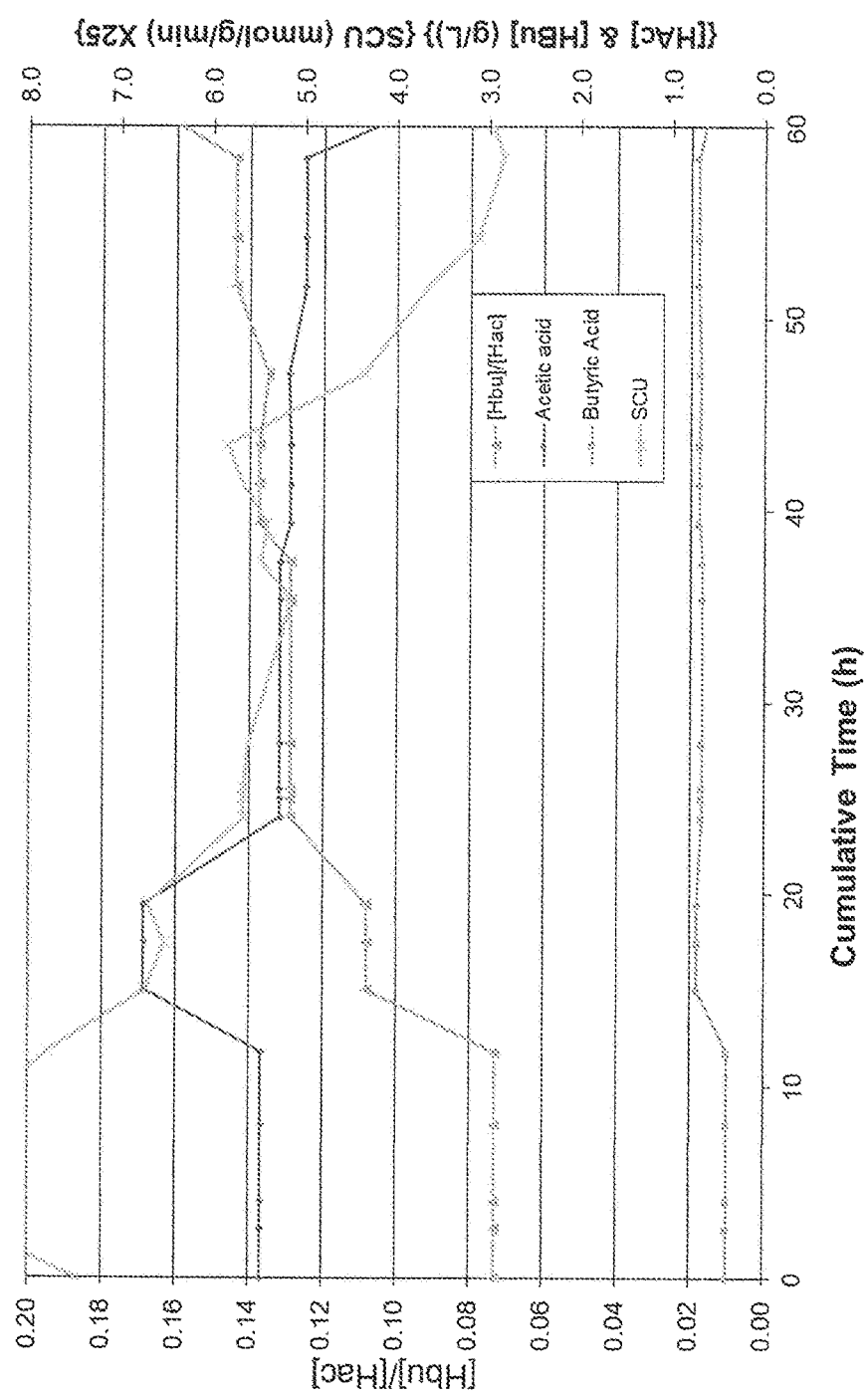
FIG. 5 describes acetic acid and butyric acid production by *Acetobacterium woodii* at pH 6.1.
Figure 6:
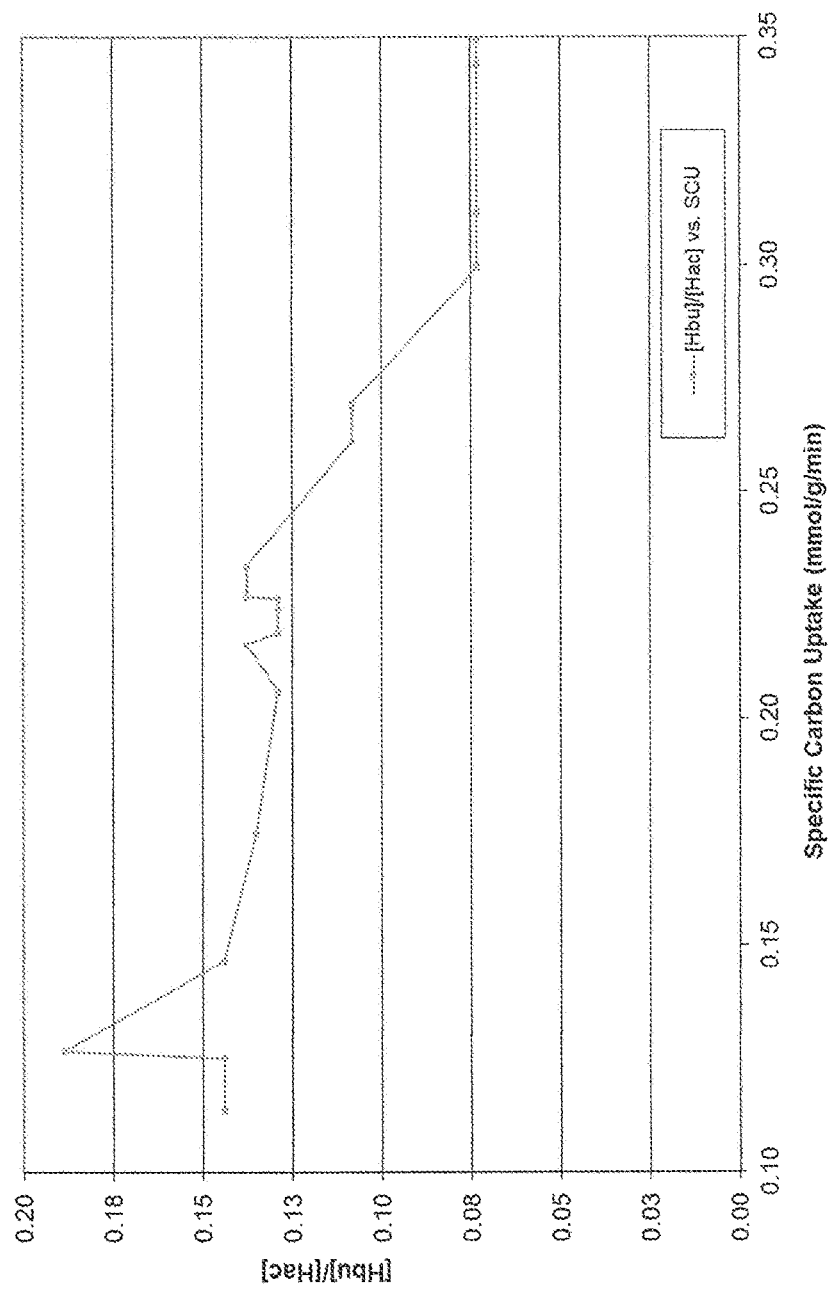
FIG. 6 shows a ratio of the concentration of butyric acid to the concentration of acetic acid versus specific carbon uptake by *Acetobacterium woodii* at pH 6.1.

FIG. 5 illustrates acetic acid and butyric acid at pH 6.1. FIG. 6 shows a ratio of the concentration of butyric acid to the concentration of acetic acid versus specific carbon uptake.

Figure 7:
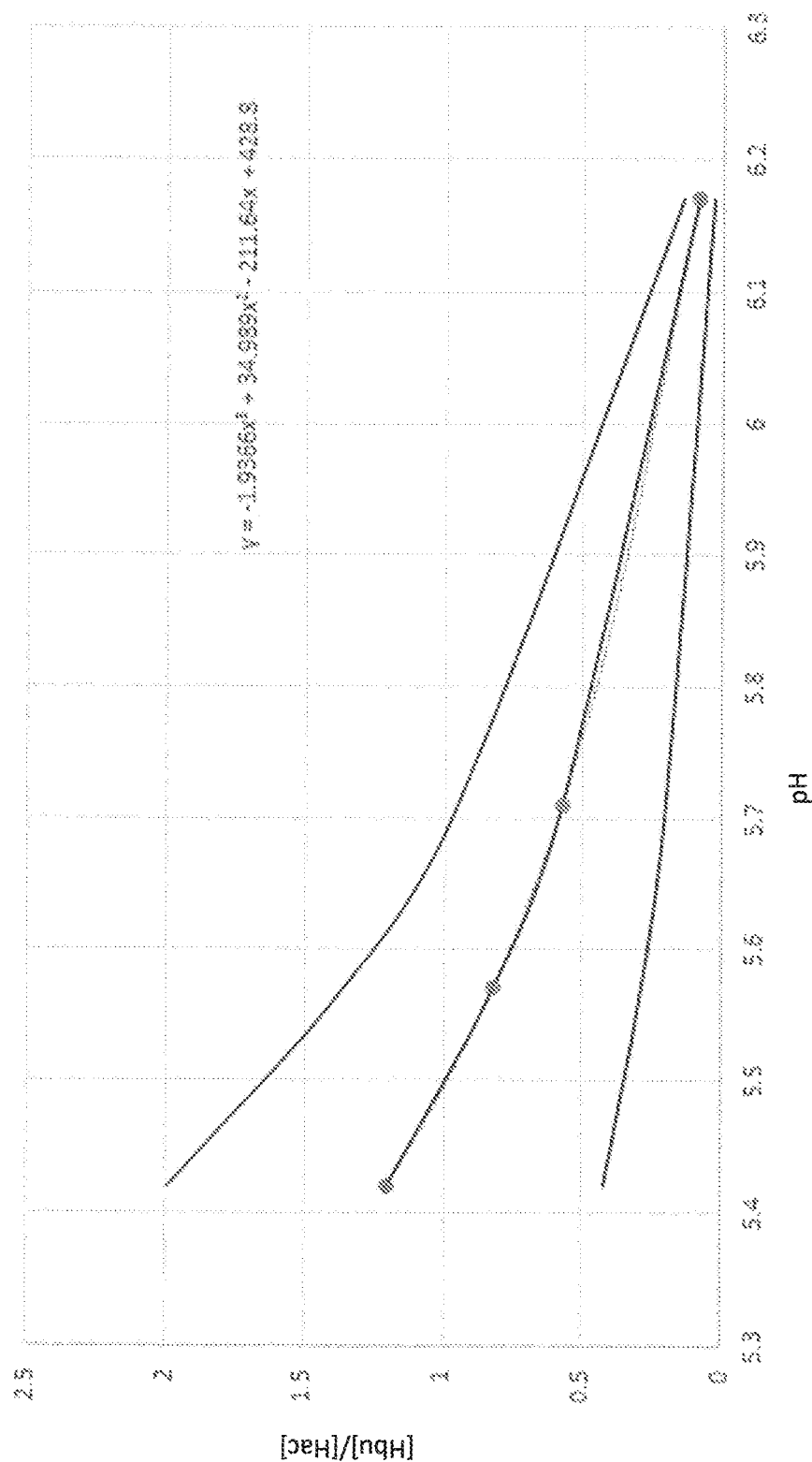
FIG. 7 illustrates a ratio of the concentration butyric acid to the concentration of acetic acid versus culture pH.

FIG. 7 shows a ratio of the concentration of butyric acid to the concentration of acetic acid versus pH. Each data point in FIG. 7 is an average of measurements of pH vs. butyric acid to acetic acid ratios. The middle line is represented by the formula $y=428.8-211.64x+34.989x^2-1.9366x^3$, where x=pH, and y is the butyric acid to acetic acid ratio. As illustrated by the outside lines, y may be in a range where $y=1.65*(428.8-211.64x+34.989x^2-1.9366x^3)$ to $y=0.35*(428.8-211.64x+34.989x^2-1.9366x^3)$. This deviation of y can be related to different bacterial species, strains and genetic modifications to the host cells. Also, different reactor conditions like temperature and pressure may effect the value of y.

The Table below set forth the data used for FIG. 7.

| pH Range | Average pH | Average Ratio ([HBu]/[HAc]) | Number of Measurements |
|---|---|---|---|
| 5.38-5.48 | 5.42 | 1.205 | 77 |
| 5.52-5.6 | 5.57 | 0.823 | 23 |
| 5.66-5.75 | 5.71 | 0.574 | 5 |
| 6.06-6.33 | 6.17 | 0.086 | 36 |

While the disclosure herein disclosed has been described by means of specific embodiments, examples and applications thereof, numerous modifications and variations could be made thereto by those skilled in the art without departing from the scope of the disclosure set forth in the claims.

What is claimed is:

1. A process comprising:
    providing a gaseous substrate comprising $CO_2$ to a bioreactor;
    providing acetogenic bacteria and medium to the bioreactor to provide a fermentation broth;
    providing sodium ions to the bioreactor through one or more sodium ion sources;
    maintaining a pH of 6 or less in the fermentation broth; and
    fermenting the gaseous substrate with the acetogenic bacteria in the fermentation broth to produce one or more organic acids;
    wherein maintaining a pH of 6 or less in the fermentation broth provides a ratio of butyric acid to acetic acid concentration of 0.2 or more,
    wherein the acetogenic bacteria includes a sodium translocating ATPase that is active during fermentation in the bioreactor, and
    wherein the sodium ions are provided so that $Na^+$ is maintained between 1000 to 11000 ppm (g/g) in the fermentation broth.

2. The process of claim 1 wherein the gaseous substrate is selected from the group consisting of industrial gases, fermentor gas streams and mixtures thereof.

3. The process of claim 1 wherein the gaseous substrate comprises a mixture of CO and $CO_2$.

4. The process of claim 3 wherein the gaseous substrate has a CO to $CO_2$ ratio of less than about 2.

5. The process of claim 1 wherein the acetogenic bacteria is selected from the group consisting of *Acetobacterium* bacteria, *Acetogenium kivui*, *Acetoanaerobium noterae*, *Acetobacterium woodii*, *Alkalibaculum bacchi* CP11 (ATCC BAA-1772), *Moorella thermoacetica*, *Moorella thermoautotrophica*, *Ruminococcus productus*, and combinations thereof.

6. The process of claim 5 wherein the acetogenic bacteria is *Acetobacterium woodii*.

7. The process of claim 1 wherein the sodium ion source is provided by a compound selected from the group consisting of sodium chloride, sodium hydroxide, sodium phosphate, sodium sulfate, sodium nitrate, sodium bicarbonate, sodium bisulfate and mixtures thereof.

8. The process of claim 1 wherein the fermentation broth includes less than about 0.01 grams per liter yeast extract, and less than about 0.01 grams per liter carbohydrate.

9. The process of claim 1 wherein the butyric acid to acetic acid ratio is determined according to a formula $y=428.8-211.64x+34.989x^2-1.9366x3$, where x=pH, and y is the butyric acid to acid ratio, wherein y is in a range where $y=1.65*(428.8-211.64x+34.989x^2-1.9366x^3)$ to $y=0.35*(428.8-211.64x+34.989x^2-1.9366x^3)$.

10. The process of claim 1 wherein the process provides a butyric acid productivity of about 0.5 grams/liter/day/g cells or more.

11. A process comprising:
    providing a gaseous substrate comprising $CO_2$ to a bioreactor;
    providing acetogenic bacteria and medium to the bioreactor to provide a fermentation broth;
    providing sodium ions to the bioreactor through one or more sodium ion sources;
    maintaining a pH of 6 or less in the fermentation broth; and fermenting the gaseous substrate with the acetogenic bacteria in the fermentation broth to produce one or more organic acids containing 3 or more carbon atoms;
wherein the acetogenic bacteria includes a sodium translocating ATPase that is active during fermentation in the bioreactor, and
wherein the sodium ions are provided so that $Na^+$ is maintained between 1000 to 11000 ppm (g/g) in the fermentation broth.

12. The process of claim 11 wherein the gaseous substrate is selected from the group consisting of industrial gases, fermentor gas streams and mixtures thereof.

13. The process of claim 11 wherein the gaseous substrate comprises a mixture of CO and $CO_2$.

14. The process of claim 11 wherein the gaseous substrate has a CO to $CO_2$ ratio of less than about 2.

15. The process of claim 11 wherein the acetogenic bacteria is selected from the group consisting of *Acetobacterium* bacteria, *Acetogenium kivui*, *Acetoanaerobium noterae*, *Acetobacterium woodii*, *Alkalibaculum bacchi* CP11 (ATCC BAA-1772), *Moorella thermoacetica*, *Moorella thermoautotrophica*, *Ruminococcus productus*, and combinations thereof.

16. The process of claim 15 wherein the acetogenic bacteria is *Acetobacterium woodii*.

17. The process of claim 11 wherein the sodium ion source is provided by a compound selected from the group consisting of sodium chloride, sodium hydroxide, sodium phosphate, sodium sulfate, sodium nitrate, sodium bicarbonate, sodium bisulfate and mixtures thereof.

18. The process of claim 11 wherein the organic acid is butyric acid or mixtures of butyric acid and propionic acid.

19. The process of claim 11 wherein the fermentation broth includes less than about 0.01 grams per liter yeast extract, and less than about 0.01 grams per liter carbohydrate.

* * * * *